(12) United States Patent
Tetreault et al.

(10) Patent No.: US 6,559,350 B1
(45) Date of Patent: May 6, 2003

(54) MOISTURE-CURABLE ADHESIVE SUTURE STRIP

(75) Inventors: Stephane Tetreault, Boucherville (CA); Simon Phaneuf, Longueuil (CA); Mahmed Benchabane, Joliette (CA)

(73) Assignee: Advanced Therapeutic Technologies At² Inc., Greenfield Park (CA)

( * ) Notice: Subject to any disclaimer, the term of this patent is extended or adjusted under 35 U.S.C. 154(b) by 0 days.

(21) Appl. No.: 09/744,597

(22) PCT Filed: Jul. 28, 1999

(86) PCT No.: PCT/CA99/00691

§ 371 (c)(1),
(2), (4) Date: Jan. 26, 2001

(87) PCT Pub. No.: WO00/06213

PCT Pub. Date: Feb. 10, 2000

(30) Foreign Application Priority Data

Jul. 28, 1998 (CA) .............................................. 2244017

(51) Int. Cl.⁷ ................................................. A61F 13/00
(52) U.S. Cl. ........................... 602/42; 602/43; 606/215; 606/216
(58) Field of Search ............................... 602/41–43, 48, 602/52, 54, 57, 60; 523/1, 105, 111, 113; 606/213, 214–216; 128/887–888

(56) References Cited

U.S. PATENT DOCUMENTS

| 3,561,441 A | * | 2/1971 | Lombardi |
| 3,645,835 A | | 2/1972 | Hodgson .................... 161/146 |
| 3,698,395 A | * | 10/1972 | Hasson |
| 4,646,731 A | * | 3/1987 | Brower |
| 4,837,062 A | * | 6/1989 | Dunshee et al. |
| 5,066,299 A | * | 11/1991 | Bellingham |
| 5,254,132 A | | 10/1993 | Barley et al. ................ 606/214 |
| 5,445,597 A | | 8/1995 | Clark et al. ................... 602/48 |
| 5,486,547 A | * | 1/1996 | Matsuda |
| 5,593,441 A | * | 1/1997 | Lichtenstein |
| 5,947,998 A | * | 9/1999 | Cartmell et al. |

FOREIGN PATENT DOCUMENTS

| WO | WO 89/07935 | 9/1989 |
| WO | WO 96/14094 | 5/1996 |
| WO | WO 97/31598 | 9/1997 |

* cited by examiner

*Primary Examiner*—Nicholas D. Lucchesi
*Assistant Examiner*—Lalita M. Hamilton
(74) *Attorney, Agent, or Firm*—Foley & Lardner

(57) ABSTRACT

A biocompatible monomer composition includes: (A) at least one monomer, which forms a medically acceptable polymer, (B) at least one plasticizing agent present in the composition in an amount of from 0.5 wt. % to 15 wt. % of the composition; and (C) at least one acidic stabilizing agent having a $pK_a$ ionization constant of from about 1 to about 7. The composition can be applied to a variety of materials and is particularly suitable as in vivo tissue adhesive. A method of joining together in vivo two surfaces, e.g., body tissues, includes (a) holding damaged tissue edges together to form abutted tissue surfaces; (b) applying to the abutted tissue surfaces an excessive amount of a composition containing 1) at least one monomer, which forms a medically acceptable biodegradable polymer, 2) at least one plasticizing agent; and 3) at least one acidic stabilizing agent; and (c) maintaining the surfaces in contact until the composition polymerizes to form a thick film of polymerized composition bridging the abutted tissue surfaces.

86 Claims, 6 Drawing Sheets

MOISTURE-CURABLE ADHESIVE SUTURE STRIP

FIELD OF THE INVENTION

The present invention pertains to improvements in the field of wound suturing. More particularly, the invention relates to a moisture-curable adhesive closing strip for closing a wound on a patient.

BACKGROUND ART

When closing a wound, it is necessary to join and keep together the facing edges of the wound. If the separated skin sections are sewn, unesthetical scars may remain, and if they are stapled, such scars generally remain.

Cyanoacrylate-based adhesives have been suggested as an alternative to sutures. When a cyanoacrylate adhesive is employed, the separated skin sections are joined and the adhesive is applied on top of the joined sections under sterile conditions. The cyanoacrylate adhesive bonds to the skin and polymerizes so as to keep together the joined sections. Although cyanoacrylate adhesives successfully bind the skin, the use of such adhesives as suture replacements can be accompanied by occasional adhesion failure resulting in wound reopening which requires closure by sutures. Fear of wound reopening is one of the reasons physicians have been reluctant to use any adhesive including cyanoacrylate-based adhesives instead of sutures.

U.S. Pat. No. 5,254,132 proposes a method of treating suturable wounds by first suturing or stapling the wound and then joining the skin between sutures or staples with a cyanoacrylate adhesive. According to this method, the wound is sutured or stapled so that the sutures or staples are separated from each other by no more than about 1.2 centimeter and no less than about 0.6 centimeter. 2-Butylcyanoacrylate is then applied to the opposing and still separated skin sections between the sutures or staples in an amount sufficient so that upon polymerization the skin sections are joined; the application is conducted so that contact of the cyanoacrylate adhesive with the sutures or staples is avoided. The adjacent separated skin sections are thereafter contacted under conditions that permit the adhesive to polymerize so as to join the separated skin sections. Such a method is not only time-consuming and requires particular skill to practice, but also delays healing of the wound if cyanoacrylate adhesive penetrates in between the skin sections.

Surgical adhesive plasters for closing wounds are also known. These plasters generally do not have much tensile strength so that their use is limited to shallow wounds requiring little tension to close. Another major disadvantage resides in their permeability to water, causing the plaster to become unstuck upon contact with water or moisture and thereby preventing the wounded area from being washed.

U.S. Pat. No. 5,259,835 discloses a wound closure device that employs a porous bonding member adapted to receive a flowable moisture-curable surgical adhesive. The bonding member is positioned by a carrier member which is used to achieve initial apposition of the wound and which may later be removed. Since the adhesive flows into the bonding member and the latter serves as a matrix for the adhesive, the bonding member becomes rigid as the adhesive therein undergoes curing so that it looses flexibility. Part of the surgical adhesive also flows through the bonding member and may enter into the wound.

DISCLOSURE OF THE INVENTION

It is therefore an object of the present invention to overcome the above drawbacks and to provide a moisture-curable adhesive suture strip for closing wounds.

According to one aspect of the invention, there is provided a moisture-curable adhesive suture strip for closing a wound on a patient, comprising:

an elongated, flexible air-permeable backing member formed of a chemically inert material and having opposite ends, first and second surfaces facing away from one another and a length and width sufficient to secure facing edges of the wound in close juxtaposition to one another, the backing member comprising a first portion disposed between the ends and adapted to overlie the facing edges of the wound, and second and third portions disposed on either side of the first portion;

a moisture-curable surgical adhesive on at least part of the first surface of the backing member including the second and third portions thereof, for adhering at least the second and third portions of the backing member to the patient with the facing edges of the wound in close juxtaposition; and a first removable protective member formed of a chemically inert material releasably secured to the backing member and covering the surgical adhesive.

After removal of the protective member to expose the adhesive and application of the backing strip with the exposed adhesive onto the patient to secure the facing edges of the wound in close juxtaposition, the adhesive upon curing together with the backing strip maintain the facing edges of the wound in close juxtaposition, without the cured adhesive adversely affecting the flexibility of the backing strip.

Applicant has found quite unexpectedly that by using a flexible and air-permeable backing member and applying on one surface of such a member a surgical adhesive, one obtains a suture strip which can be easily and rapidly applied onto the patient to secure the facing edges of the wound in close juxtaposition with one another, without the adhesive entering into the wound and delaying healing thereof. The adhesive upon curing together with the backing member maintain the facing edges of the wound in close juxtaposition, thereby preventing adhesion failure and reopening of the wound. Since the flexibility of the backing member is not adversely affected by the cured adhesive, the suture strip remains flexible and can thus follow movements of the skin. The backing member is of course air-permeable to enable the skin to breathe. Examples of suitable surgical adhesives which can be used include cyanoacrylates such as 2-n-butylcyanoacrylate and 2-octylcyanoacrylate. The curing time of 2-n-butylcyanoacrylate is about 30 seconds, whereas that of 2-octylcyanoacrylate is about 60 seconds. Preferably, the surgical adhesive comprises a cyanoacrylate in admixture with a stabilizing agent such as sulfurous acid.

The expression "chemically inert material" as used herein refers to a material which does not react with the surgical adhesive to cause curing thereof during storage of the suture strip. Examples of suitable chemically inert material include polyethylene and tetrafluoroethylene. When the backing member is formed of polyethylene, use is preferably made of a low density polyethylene or a blend of low density polyethylene and high density polyethylene. The protective member, on the other hand, preferably comprises a film of high density polyethylene.

According to a preferred embodiment of the invention, a layer of surgical adhesive completely covers the first surface of the backing member. Preferably, the backing member comprises a canvas of chemically inert material having at the first surface cavities filled with the surgical adhesive to provide an anchoring of the backing member to the patient.

According to another preferred embodiment, a plurality of spaced-apart dots of surgical adhesive are provided only on the second and third portions of the backing member. Preferably, a pressure-sensitive adhesive is provided on the first surface of the backing member between the dots of surgical adhesive, the protective member covering the pressure-sensitive adhesive.

According to a further preferred embodiment, a plurality of spaced-apart strips of surgical adhesive are provided only on the second and third portions of the backing member, the strips of surgical adhesive extending transversely of the backing member. Preferably, a pressure-sensitive adhesive is provided on the first surface of the backing member between the strips of surgical adhesive, the protective member covering the pressure-sensitive adhesive.

Generally, the dots or strips of surgical adhesive define a total area representing from about 10 to about 50%, preferably from about 15 to about 30%, of the area defined by the first surface of the backing member.

According to yet another preferred embodiment, a finger-grip tab is detachably connected to the backing member at one of the ends thereof along a tear-line extending transversely of the backing member. Such a tab enables one to pull the backing member away from the protective member and thereby remove the latter to expose the adhesive on the backing member. After the suture strip has been applied onto the patient's skin, the tab is torn away. Preferably, the protective member is substantially coextensive with the backing member along the length thereof and the tab, and extends beyond opposite side edges of the backing member and tab.

According to still a further preferred embodiment, a second removable protective member having a pressure-sensitive adhesive on one side thereof is releasably secured to the backing member and covers the second surface thereof, the backing member being disposed between the first and second protective members. Instead of using a second pressure-sensitive adhesive, it is also possible to removably attach the second protective member to the backing member by heat or pressure application. Examples of suitable pressure-sensitive adhesives which may be used include rubber or oil-based adhesives. The second protective member preferably comprises a film of low density polyethylene. Preferably, each of the first and second protective members extends beyond opposite end edges and opposite side edges of the backing member to define respective first and second end portions and first and second lateral portions. The first end portions and the first and second lateral portions of the first and second protective members face one another and are releasably bonded together by the pressure-sensitive adhesive or any other suitable method. The second end portion of the second protective member faces the second end portion of the first protective member and is partially free of adhesive so as to define with the second end portion of the first protective member a pair of finger-grip tabs.

The present invention also provides, in another aspect thereof, a moisture-curable adhesive suture strip comprising:

an elongated, flexible air-permeable backing member having opposite ends, first and second surfaces facing away from one another and a length and width sufficient to secure facing edges of the wound in close juxtaposition to one another, the backing member comprising a first portion disposed between the ends and adapted to overlie the facing edges of the wound, and second and third portions disposed on either side of the first portion;

a plurality of spaced-apart rupturable spherules secured to the first surface of the backing member and disposed on at least the second and third portions thereof, the spherules each comprising a rupturable membrane formed of a chemically inert material and encapsulating a flowable, moisture-curable surgical adhesive, and being adapted to release upon rupture of the membranes the surgical adhesive onto part of the first surface of the backing member including the second and third portions thereof;

a pressure-sensitive adhesive on the first surface of the backing member between the spherules for adhering at least the second and third portions of the backing member to the patient with the facing edges of the wound in close juxtaposition, prior to rupture of the spherules; and a removable protective member releasably secured to the backing member and covering the spherules and the pressure-sensitive adhesive.

After removal of the protective member to expose the spherules and the pressure-sensitive adhesive, application of the backing member with the exposed spherules and pressure-sensitive adhesive onto the patient to secure the facing edges of said wound in close juxtaposition and application of pressure onto the second surface of the backing member to cause rupture of the spherules and release of the surgical adhesive therefrom, the surgical adhesive flows on part of the first surface of the backing member and upon curing forms discrete bonding sites strengthening the adhesion of at least the second and third portions of the backing member to the patient and cooperating with the backing member to maintain the facing edges of the wound in close juxtaposition without the cured adhesive adversely affecting the flexibility of the backing member.

The above suture strip featuring rupturable spherules comprising a rupturable membrane formed of a chemically inert material and encapsulating the surgical adhesive avoids having to use a backing member and a protective member formed of a chemically inert material. For example, the backing member can be formed of polyurethane or nylon. Use can also be made of a backing member comprising a web of fabric material. The protective member, on the other hand, can comprise a sheet of wax paper. However, a protective member comprising a film of high density polyethylene is preferred.

According to a preferred embodiment, the spherules are provided only on the second and third portions of the backing member.

According to another preferred embodiment, a portion of the first surface of the backing member surrounding each spherule is free of pressure-sensitive adhesive for receiving the surgical adhesive released from the spherule upon rupturing.

Instead of securing the spherules to the backing member, it is possible to secure the spherules to the protective member. The present invention therefore provides, in a further aspect thereof, a moisture-curable adhesive suture strip comprising:

an elongated, flexible air-permeable backing member having opposite ends, first and second surfaces facing away from one another and a length and width sufficient to secure facing edges of the wound in close juxtaposition to one another, the backing member comprising a first portion disposed between the ends and adapted to overlie the facing edges of the wound, and second and third portions disposed on either side of the first portion;

a pressure-sensitive adhesive on at least part of the first surface of the backing member including the second and third portions thereof, for adhering at least the second and third portions of the backing member to the patient with the facing edges of the wound in close juxtaposition;

a removable protective member releasably secured to the backing member and covering the pressure-sensitive adhesive, the protective member having first and second surfaces facing away from one another with the first surface facing the first surface of the backing member; and a plurality of spaced-apart rupturable spherules disposed between the backing member and the protective member and secured to the first surface of the protective member, the spherules each comprising a rupturable membrane formed of a chemically inert material and encapsulating a flowable, moisture-curable surgical adhesive, and being disposed on the protective member at predetermined locations so as to release upon rupture of the membranes the surgical adhesive onto part of the first surface of the backing member including the second and third portions thereof.

After application of pressure onto the second surface of the backing member or protective member to cause rupture of the spherules and release of the surgical adhesive therefrom, removal of the protective member to expose the pressure-sensitive adhesive and the surgical adhesive released on part of the first surface of the backing member and application of the backing member with the exposed pressure-sensitive adhesive and surgical adhesive onto the patient to secure the facing edges of the wound in close juxtaposition, the surgical adhesive upon curing forms discrete bonding sites strengthening the adhesion of at least the second and third portions of the backing member to the patient and cooperating with the backing member to maintain the facing edges of the wound in close juxtaposition without the cured adhesive adversely affecting the flexibility of the backing member.

According to a preferred embodiment, the spherules are disposed on the protective member opposite only the second and third portions of the backing member.

According to another preferred embodiment, a portion of the first surface of the backing member opposite each spherule is free of pressure-sensitive adhesive for receiving the surgical adhesive released from the spherule upon rupturing.

According to yet another preferred embodiment, the spherules whether secured to the backing member or protective member have a diameter ranging from about 0.5 to about 3 mm, preferably from 1 to 2 mm. Generally, the spherules define a total area representing from about 10 to about 50%, preferably from about 15 to about 30%, of the area defined by the first surface of the backing member.

DESCRIPTION OF THE DRAWINGS

Further features and advantages of the present invention will become more readily apparent from the following description of preferred embodiments as illustrated by way of examples in the accompanying drawings, in which.

MODES FOR CARRYING OUT THE INVENTION

Figure 1:
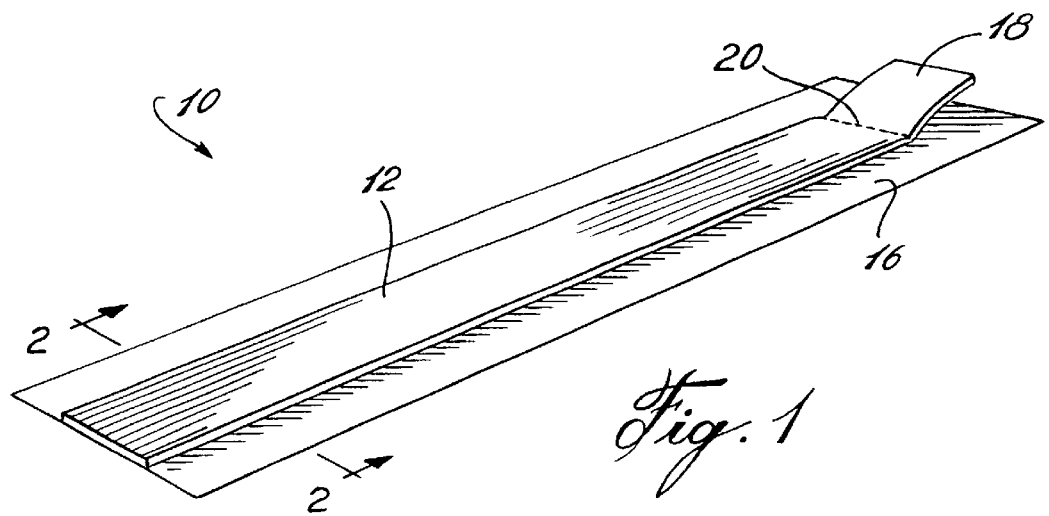
FIG. 1 is a perspective view of a moisture-curable adhesive suture strip according to a preferred embodiment of the invention.
Figure 2:
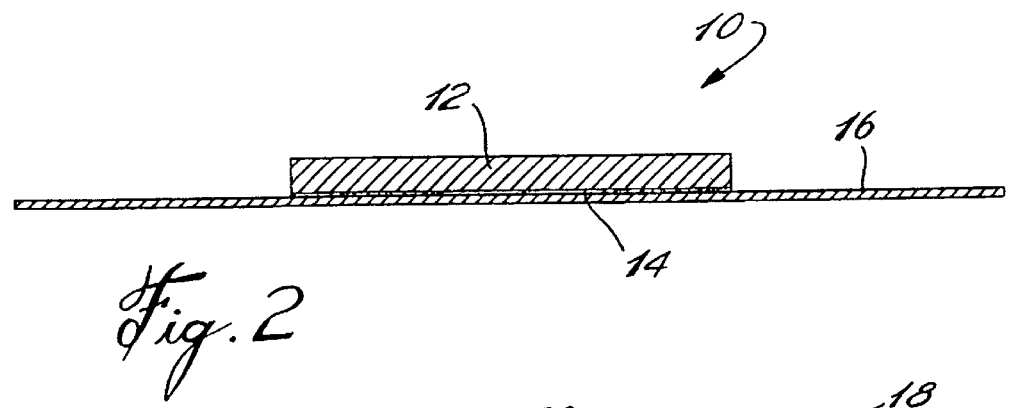
FIG. 2 is a sectional view taken along line 2—2 of FIG. 1.

Referring first to FIGS. 1 and 2, there is illustrated a moisture-curable adhesive suture strip which is generally designated by reference numeral 10 and used for closing a wound on a patient (not shown). The suture strip 10 comprises an elongated, flexible and air-permeable backing member 12 having a wound facing surface coated with a surgical adhesive 14. The backing member 12 has a length and width sufficient to secure facing edges of the wound in close juxtaposition to one another. A protective member 16 is removably attached to the backing member 12 and covers the adhesive 14. Both the backing member 12 and protective member 16 are formed of a chemically inert material. A finger-grip tab 18 is detachably connected to the backing member 12 at one end thereof along a tear-line 20 extending transversely of the member 12. As shown, the protective member 16 is substantially coextensive with the backing member 12 along the length thereof and the tab 18, and extends beyond opposite side edges of the member 12 and tab 18.

In use, the protective member 16 is first peeled-off to expose the adhesive 14 while holding the tab 18 with one's fingers. The end portion of the backing member 12 opposite the tab 18 is adhered to one of the separated skin sections, which is then pulled in a direction towards the other separated skin section to bring the facing edges of the wound in close juxtaposition with one another, and the other end portion of the member 12 adjacent the tab 18 is adhered to the other skin section, thereby closing the wound and securing the facing edges thereof in close juxtaposition. The tab 18 is thereafter torn along the tear-line 20.

Figure 3:
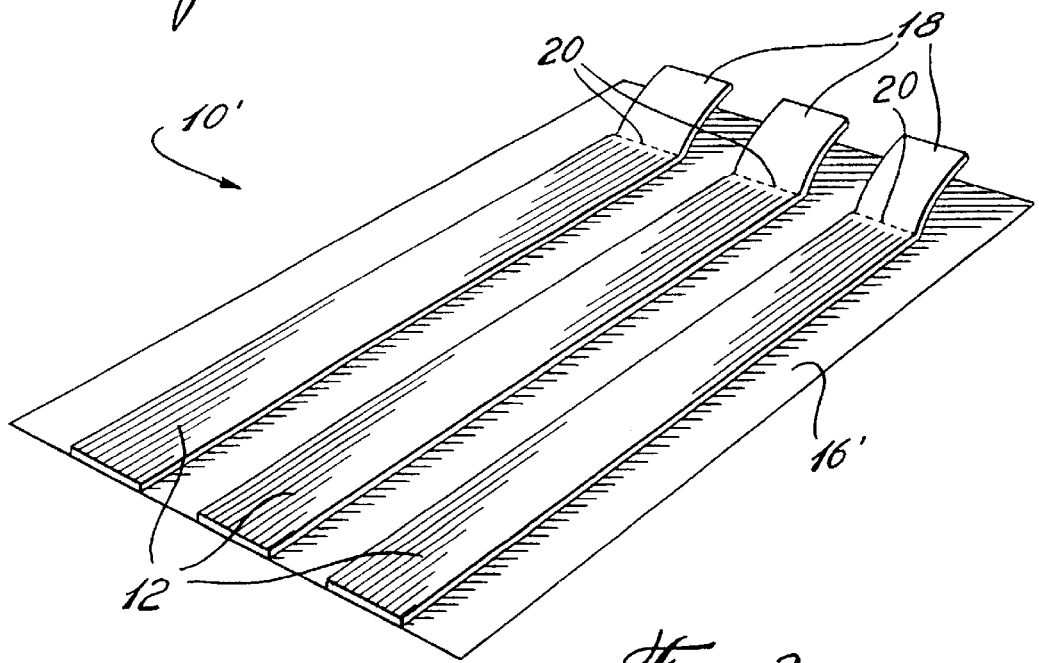
FIG. 3 is a perspective view of moisture-curable adhesive suture strip according to another preferred embodiment of the invention.

The embodiment 10' illustrated in FIG. 3 is similar to that shown in FIG. 1, with the exception that a much wider protective member 16' is used to accommodate a plurality of backing member 12 coated with surgical adhesive.

Figure 4:
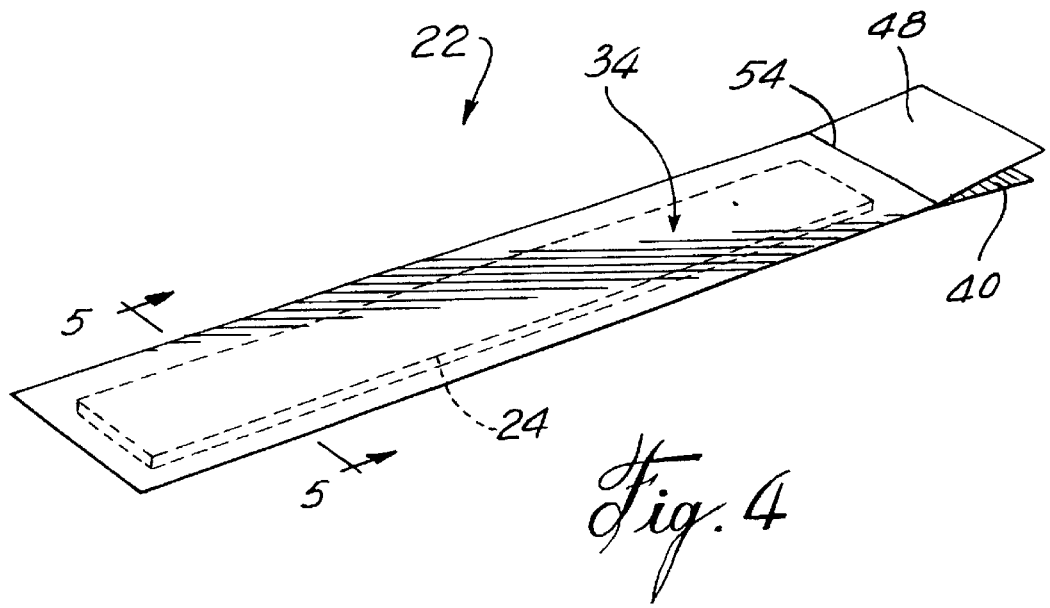
FIG. 4 is a perspective view of a moisture-curable adhesive suture strip according to a further preferred embodiment of the invention.
Figure 5:
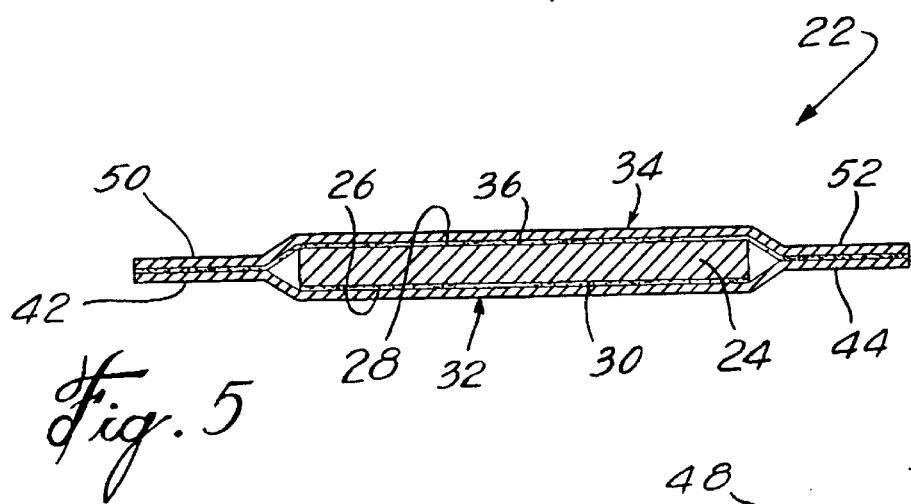
FIG. 5 is a sectional view taken along line 5—5 of FIG. 4.
Figure 6:
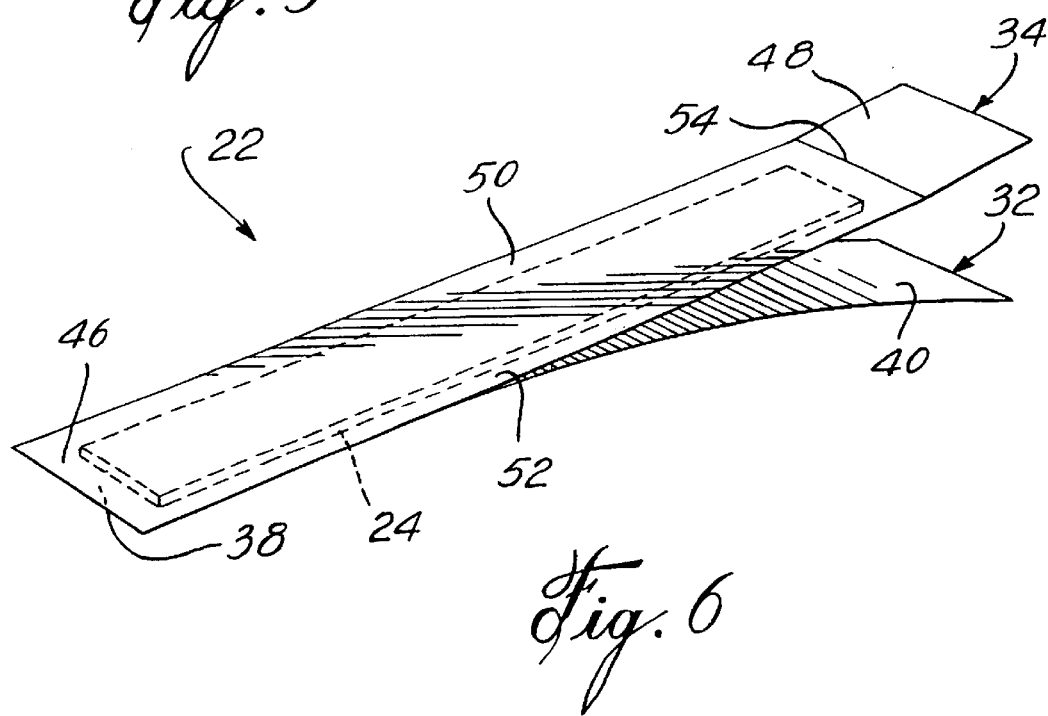
FIG. 6 is a view illustrating how the lower protective member is peeled-off the suture strip of FIG. 4 to expose the adhesive coating on the backing strip.

Turning to FIGS. 4 to 6, there is illustrated another moisture-curable adhesive suture strip which is generally designated by reference numeral 22 and comprises an elongated, flexible and air-permeable backing member 24 having surfaces 26 and 28 facing away from one another with the surface 26 being coated with a surgical adhesive 30. The backing member 24 has a length and width sufficient to secure facing edges of the wound in close juxtaposition to one another. A protective member 32 is removably attached to the backing member 24 and covers the adhesive 30. Both the backing member 24 and protective member 32 are formed of a chemically inert material. A further protective member 34 having a pressure-sensitive adhesive 36 coated on one side thereof is removably attached to the backing member 24 and covers the surface 28. The protective member 34 may be also attached to the backing member 24 by means other than adhesives, e.g. heat or pressure applications. As shown, the member 24 is disposed between the protective members 32 and 34.

The protective member 32 extends beyond the end edges and side edges of the backing member 24 to define end portions 38,40 and lateral portions 42,44. Similarly, the protective member 34 extends beyond the end edges and side edges of the backing strip 24 to define end portions 46,48 and lateral portions 50,52. The end portions 38,46 and lateral portions 42,50 and 44,52 face one another and are releasably bonded together by the adhesive 36 (or other). The end portion 48 is partially free of adhesive so as to define with the end portion 40 a pair of finger-grip tabs, the tab defined by the end portion 48 being foldable along the fold line 54.

FIG. 6 illustrates how the protective member 32 is peeled-off to expose the adhesive 30 on the backing member 24. The member 24 with the exposed adhesive 30, carrying the protective member 34, is used in the same manner as the suture strip 10 shown in FIGS. 1–3 to close a wound. After the facing edges of the wound have been secured in close juxtaposition to one another, the protective member 34 is peeled-off.

Figure 7:
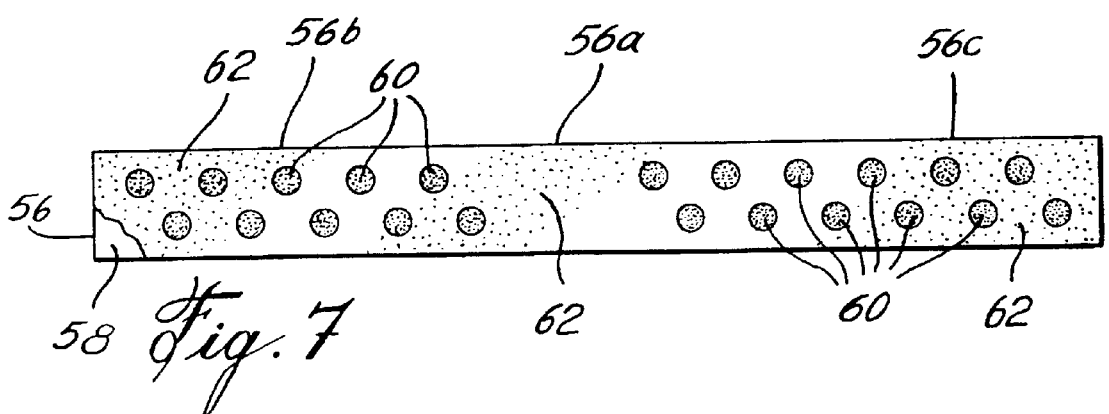
FIG. 7 is a fragmentary bottom plan view of a backing member according to a preferred embodiment, shown provided with a plurality of spaced-apart dots of surgical adhesive.
Figure 8:
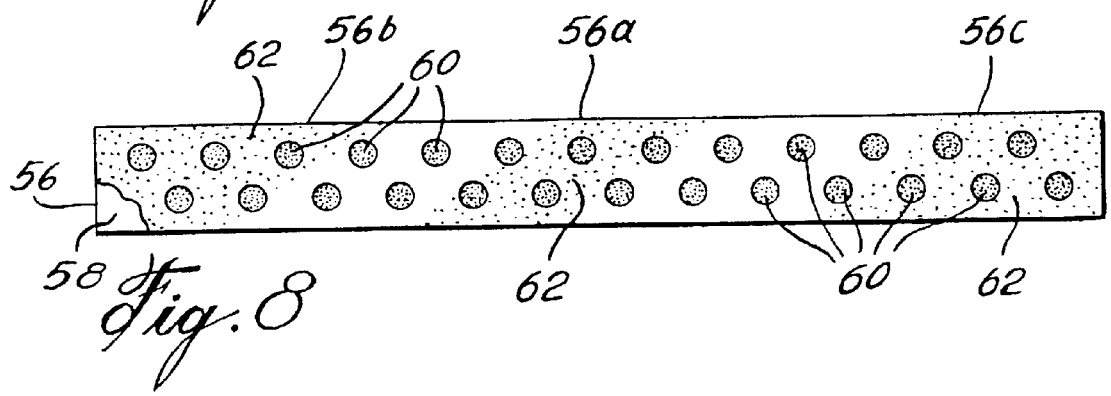
FIG. 8 is a fragmentary bottom plan view of a backing member according to another preferred embodiment, shown also provided with a plurality of spaced-apart dots of surgical adhesive.

Turning to FIGS. 7 and 8, there is illustrated a backing member 56 which is similar to the backing member 12 or 24 shown in FIGS. 1–3 and FIGS. 4–6, and which can form part of the suture strip 10,10' or 22. Instead of having a continuous coating of surgical adhesive, the backing member 56 is provided on its wound facing surface 58 with a plurality of spaced-apart dots 60 of surgical adhesive. The backing member 56 has a substantially central portion 56a adapted to overlie the facing edges of a wound and two portions 56b,56c disposed on either side of the portion 56a. In the embodiment of FIG. 7, the dots 60 of surgical adhesive are provided only on the portions 56b and 56c of the backing member 56 whereas, in the embodiment of FIG. 8, they are provided on all portions 56a, 56b and 56c. A pressure-sensitive adhesive 62 is also provided on the surface 58 between the dots 60 of surgical adhesive.

Figure 9:
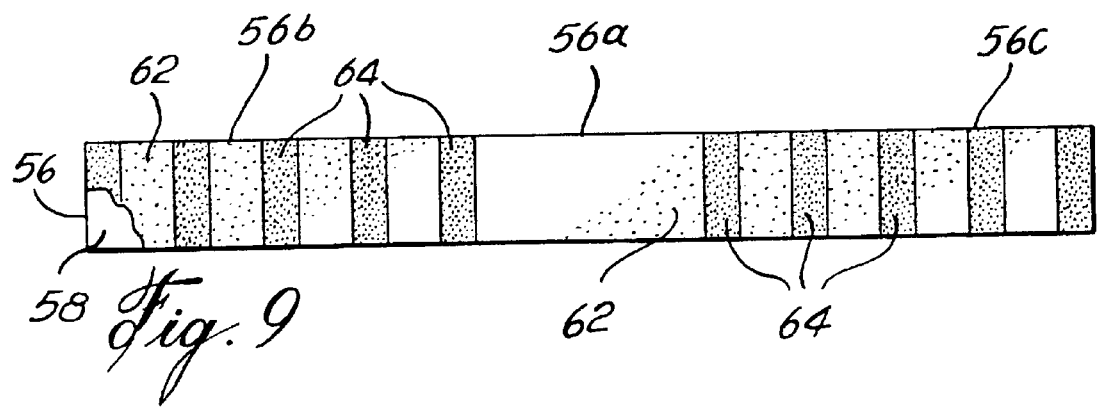
FIG. 9 is a fragmentary bottom plan view of a backing member according to a further preferred embodiment, shown provided with a plurality of spaced-apart strips of surgical adhesive.
Figure 10:
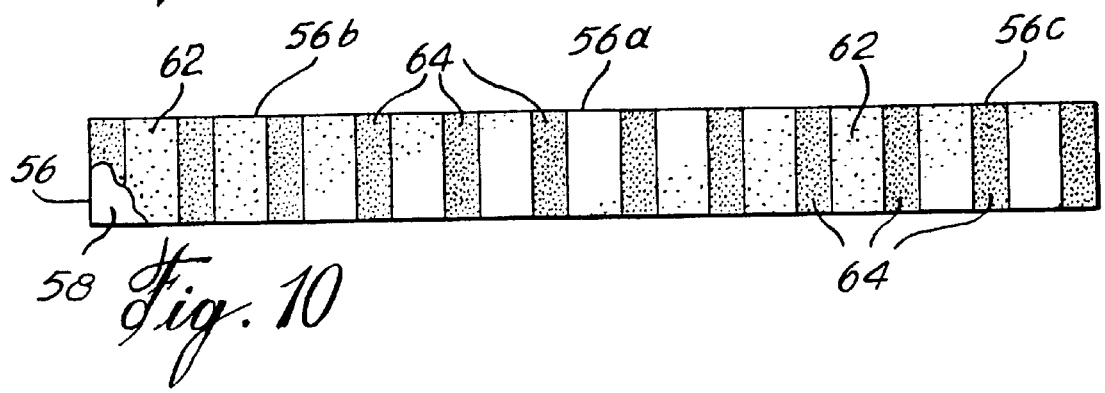
FIG. 10 is a fragmentary bottom plan view of a backing member according to yet another preferred embodiment, shown also provided with a plurality of spaced-apart strip of surgical adhesive.

The embodiments illustrated in FIGS. 9 and 10 are similar to those illustrated in FIGS. 7 and 8, respectively, with the exception that instead of dots of surgical adhesive a plurality of spaced-apart strips 64 of surgical adhesive are provided on the surface 58 of the backing member 56. As shown, the strips 64 of surgical adhesive extend transversely of the backing member 56.

Figure 11:
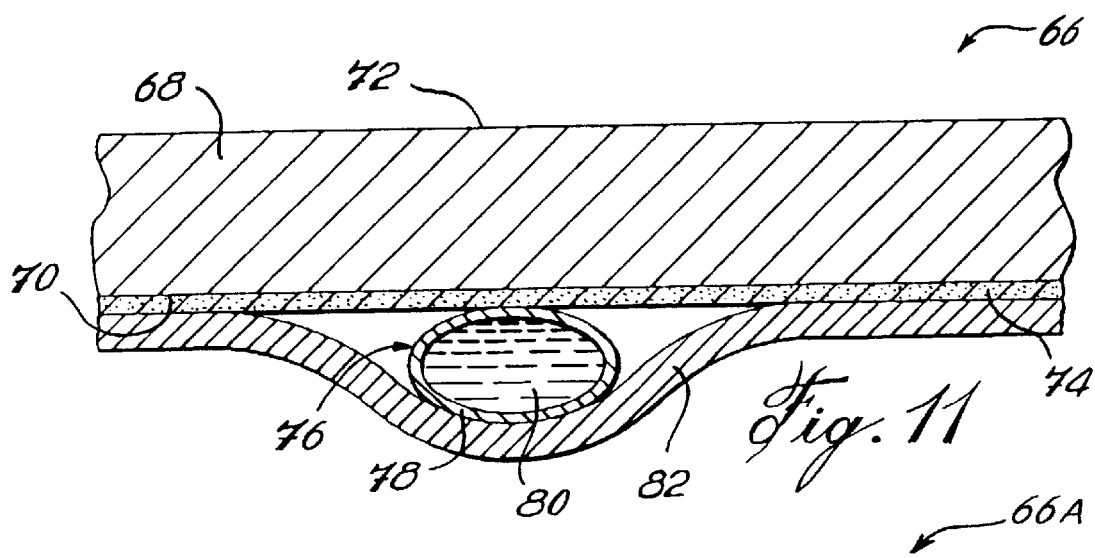
FIG. 11 is a partial sectional view of a suture strip according to yet another preferred embodiment of the invention.
Figure 13:
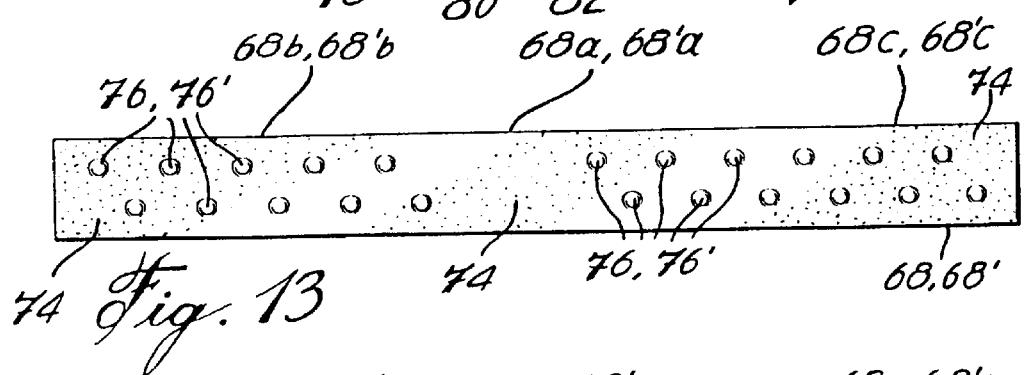
FIG. 13 is a bottom plan view of the suture strip illustrated in FIGS. 11 or 12 and shown without its protective member.
Figure 14:
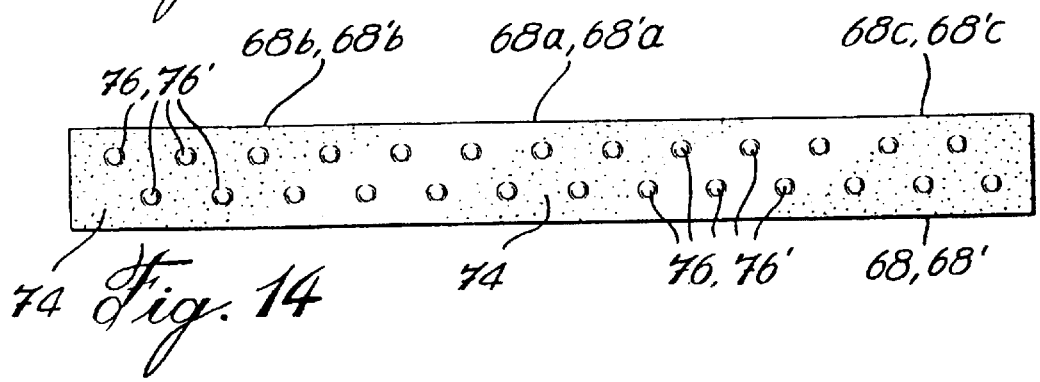
FIG. 14 is a view similar to FIG. 13, showing a variant of the suture strip illustrated in FIGS. 11 or 12.

Turning to FIGS. 11, 13 and 14, there is illustrated a further moisture-curable adhesive suture strip which is generally designated by reference numeral 66 and comprises an elongated, flexible and air-permeable backing member 68 having surfaces 70 and 72 facing away from one another with the surface 70 being coated with a pressure-sensitive adhesive 74. The backing member 68 has a length and width sufficient to secure facing edges of a wound in close juxtaposition to one another. The member 68 has a substantially central portion 68a adapted to overlie the facing edges of the wound, and two portions 68b,68c disposed on either side of the portion 68a. A plurality of spaced-apart rupturable spherules 76 are secured to the surface 70 of the backing member 68 by means of the pressure-sensitive adhesive 74. In the embodiment of FIG. 13, the spherules 76 are disposed only on the portions 68b and 68c of the backing member 68 whereas, in the embodiment of FIG. 14, they are disposed on all portions 68a, 68b and 68c. Each spherule 76 comprises a rupturable membrane 78 formed of a chemically inert material and encapsulating a flowable, moisture-curable surgical adhesive 80. The spherules 76 are adapted to release upon rupture of the membranes 78 the surgical adhesive 80 onto the coated surface 70. A removable protective member 82 is releasably secured to the backing member 68 and covers the pressure-sensitive adhesive 74 and the spherules 76.

Figure 12:
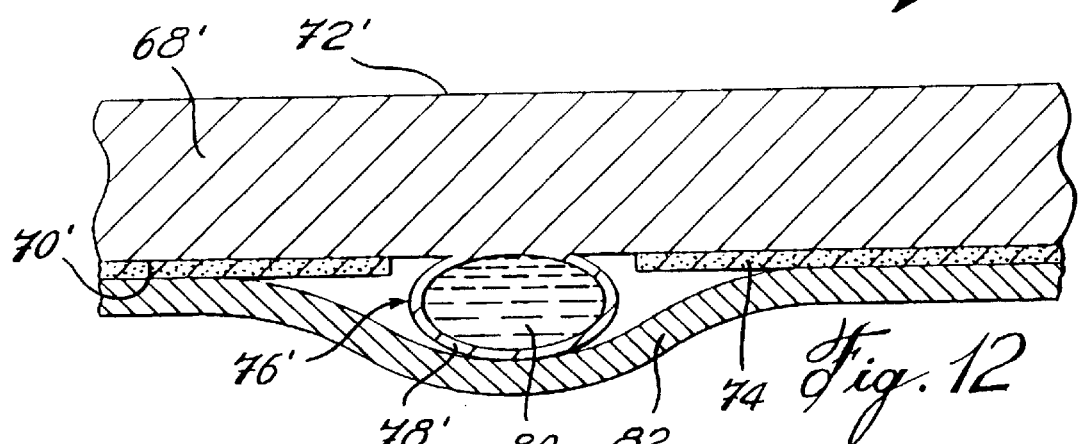
FIG. 12 is a partial sectional view of a suture strip according to still another preferred embodiment of the invention.

The suture strip 66A illustrated in FIG. 12 is similar to the strip 66 shown in FIG. 11, with the exception that the membrane 78' of each spherule 76' is integrally formed with the backing member 68', thereby securing the spherule 76' to the surface 70'. In such an embodiment, the backing member 68' is of course formed of a chemically inert material. The disposition of the spherules 76' on the backing member 68' is shown in FIGS. 13 and 14.

In use, the protective member 82 is first peeled-off to expose the pressure-sensitive adhesive 74 and spherules 76,76' and one of the portions 68b,68c or 68'b,68'c of the backing member 68,68' with the exposed adhesive 74 and spherules 76,76' is adhered to one of the separated skin sections, which is then pulled in a direction towards the other separated skin section to bring the facing edges of the wound in close juxtaposition to one another, and the other potion of the member 68,68' is adhered to the other skin section, thereby closing the wound and securing the facing edges thereof in close juxtaposition. Pressure is then applied onto the surface 72,72' of the backing member 68,68' to cause rupture of the spherules 76,76' and release of the surgical adhesive 80 therefrom. The adhesive 80 flows on part of the coated surface 70,70' of the backing member 68,68' and upon curing forms discrete bonding sites strengthening the adhesion of the portions 68b,68c or 68'b, 68'c of the backing member 68,68' to the patient's skin and cooperating with the member 68,68' to maintain the facing edges of the wound in close juxtaposition without the cured adhesive adversely affecting the flexibility of the member 68,68'.

Figure 15:
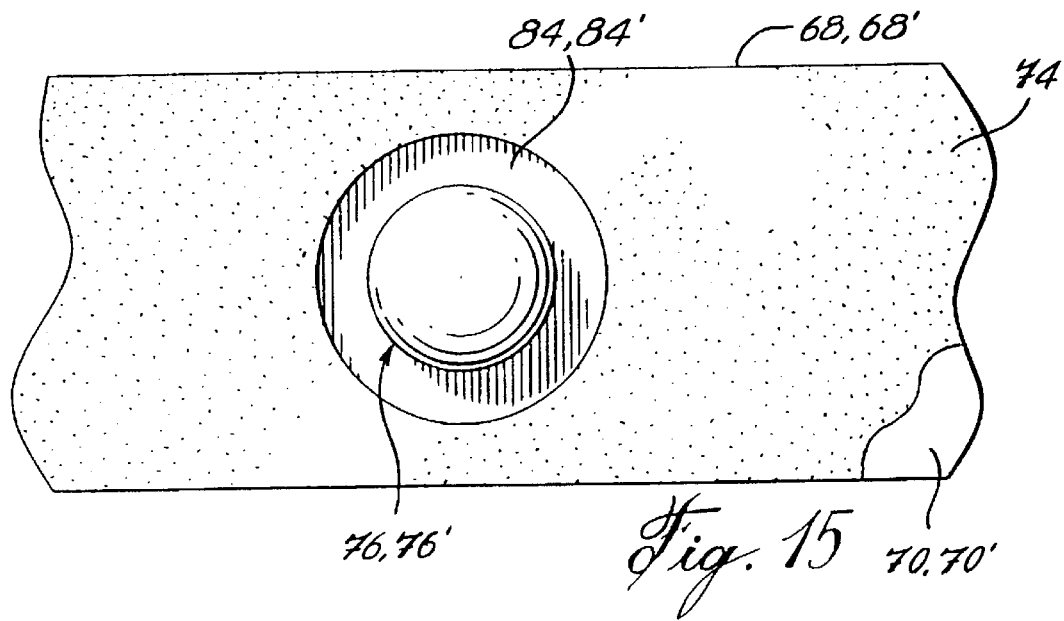
FIG. 15 is a partial bottom plan view of another variant of the suture strip illustrated in FIG. 11 or 12 and shown without its protective member.

In the embodiment illustrated in FIG. 15, a portion 84 or 84' of the surface 70 or 70' surrounding each spherule 76,76' is free of pressure-sensitive adhesive 74 for receiving the surgical adhesive 80 released by the spherule 76,76' upon rupturing.

Figure 16:
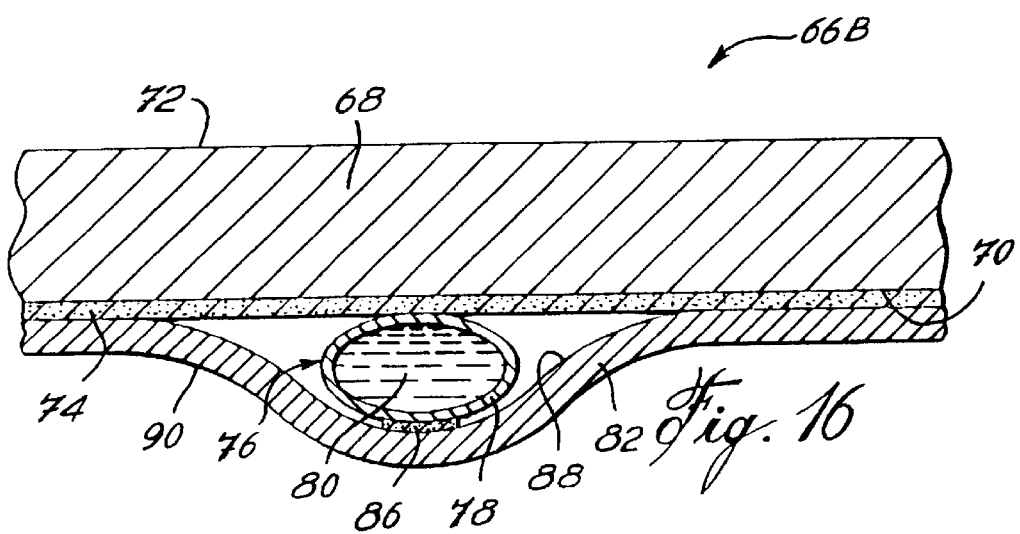
FIG. 16 is a partial sectional view of a suture strip according to yet a further preferred embodiment of the invention.
Figure 18:
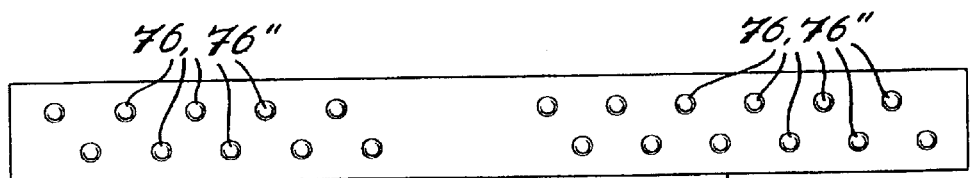
FIG. 18 is a top plan view of the protective member illustrated in FIGS. 16 or 17, and shown provided with a plurality of spaced-apart spherules.

The suture strip 66B illustrated in FIG. 16 is similar to the strip 66 shown in FIG. 11, with the exception that the spherules 76 are secured with adhesive 86 to the surface 88 of the protective member 82. The adhesive 86 is preferably a pressure-sensitive adhesive. In the embodiment of FIG. 18, the spherules 76 are disposed on the protective member 82 opposite only the portions 68b and 68c of the backing member 68 shown in FIG. 13 whereas, in the embodiment of FIG. 19, they are disposed on the protective member 82 opposite all portions 68a, 68b and 68c.

Figure 17:
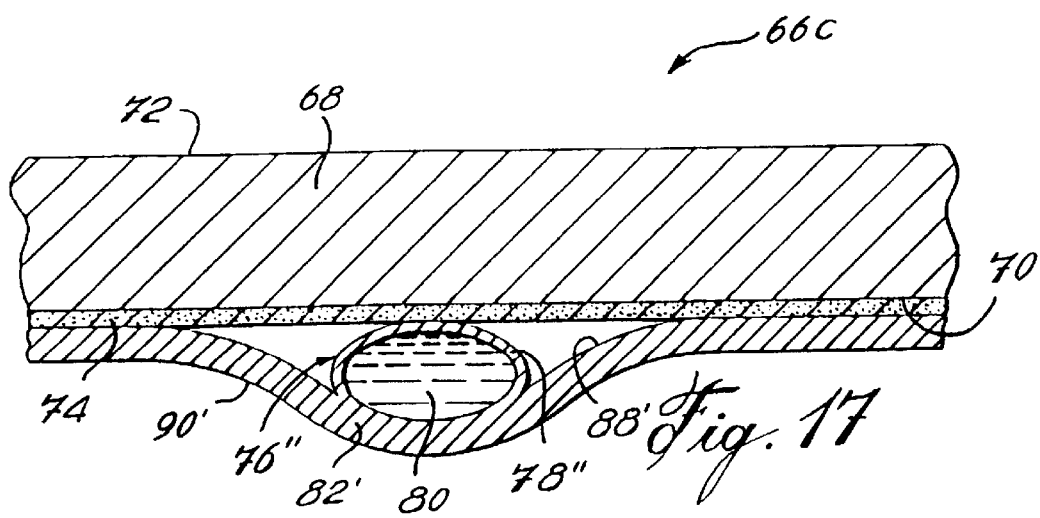
FIG. 17 is a partial sectional view of a suture strip according to still a further preferred embodiment of the invention.
Figure 19:
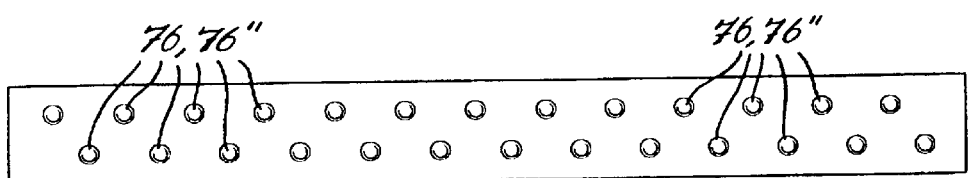
FIG. 19 is a view similar to FIG. 18, showing a different arrangement of the spherules.

The suture strip 66C illustrated in FIG. 17 is similar to the strip 66B shown in FIG. 16, with the exception that the membrane 78" of each spherule 76" is integrally formed with the protective member 82', thereby securing the spherule 76" to the surface 88'. In such an embodiment, the protective member 82' is of course formed of a chemically inert material. The disposition of the spherules 76" on the protective member 82' is shown in FIGS. 18 and 19.

In use, pressure is applied onto the surface 72 of the backing member and/or the surface 90,90' of the protective member 82,82' to cause rupture of the spherules 76,76" and release of the surgical adhesive 80 therefrom, the protective member 82,82' is peeled-off to expose the pressure-sensitive adhesive 74 and the surgical adhesive 80 released on part of the coated surface 70 of the backing member 68 and one of the portions 68b,68c of the member 68 with the exposed adhesives 74 and 80 is adhered to one of the separated skin sections, which is then pulled in a direction towards the other separated skin section to bring the facing edges of the wound in close juxtaposition to one another, and the other portion of the member 68 is adhered to the other skin section, thereby closing the wound and securing the facing edges thereof in close juxtaposition. The surgical adhesive 80 upon curing forms discrete bonding sites strenghtening the adhesion of the portions 68b and 68c of the backing member 68 to the patient's skin and cooperating with the member 68 to maintain the facing edges of the wound in close juxtaposition without the cured adhesive adversely affecting the flexibility of the member 68.

Figure 20:
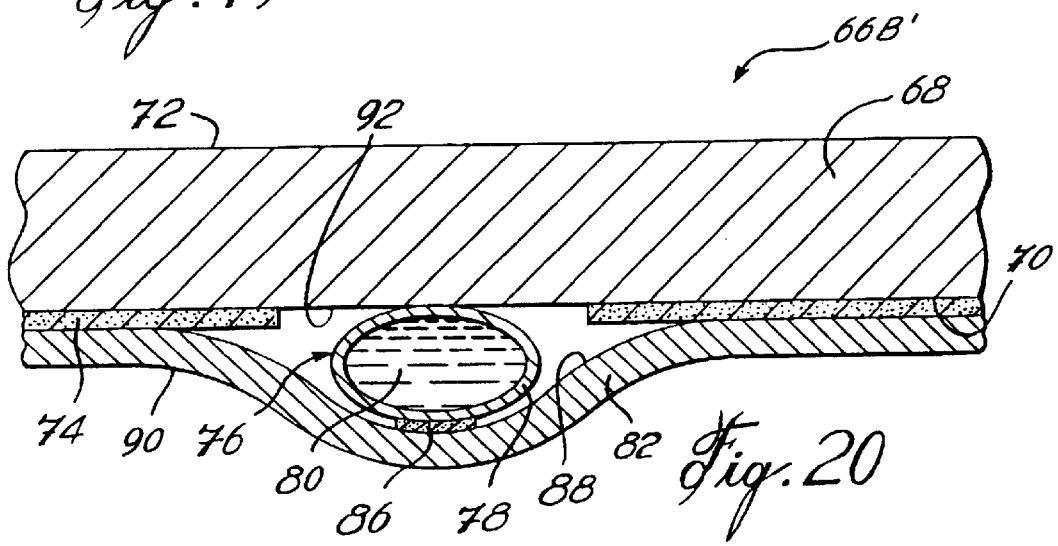
FIGS. 20 and 21 are views similar to FIGS. 16 and 17, showing variants of the suture strip.
Figure 21:
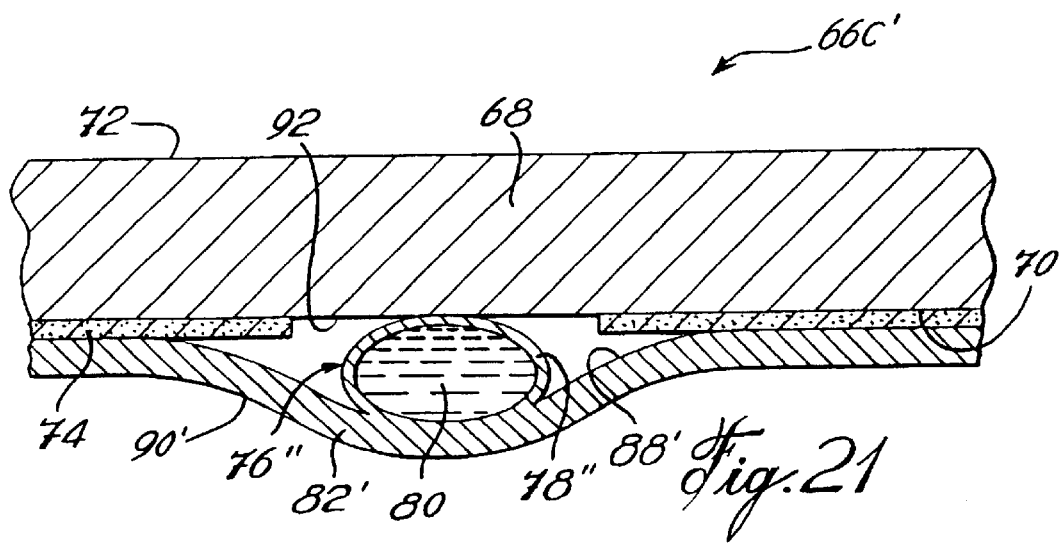

In the embodiments 66B' and 66C' illustrated in FIGS. 20 and 21, a portion 92 of the surface 70 of the backing member opposite each spherule 76,76" is free of pressure-sensitive adhesive 74 for receiving the surgical adhesive 80 released by the spherule 76,76" upon rupturing.

The backing members 68 and 68' can be provided with a tab similar to the tab 18 shown in FIG. 1. The protective members 82 and 82' can also extend beyond the end edges and side edges of the backing member to define end and lateral portions similar to the end portions 38,40 and lateral portions 42,44 shown in FIGS. 5 and 6, and a second removable protective member similar to the protective member 34 shown in FIGS. 4–6 can be releasably secured with pressure-sensitive adhesive (or other suitable means, as mentioned hereinbefore) to the surface 72,72' of the backing member 68,68' for the same purpose as discussed in respect of FIGS. 4–6.

What is claimed is:

1. A moisture-curable adhesive suture strip for closing a wound on a patient, comprising:

an elongated, flexible air-permeable backing member formed of a chemically inert material, and having opposite ends, first and second surfaces facing away from one another and a length and width adapted to secure facing edges of the wound in close juxtaposition to one another, said backing member comprising a first portion disposed between said ends and adapted to overlie the facing edges of said wound, and second and third portions disposed on either side of said first portion;

a moisture-curable surgical adhesive on at least part of the first surface of said backing member including said second and third portions thereof, in spaced-apart discrete areas of said first surface;

a pressure-sensitive adhesive on the first surface of said backing member between said discrete areas for adhering at least said second and third portions of said backing member to the patient with the facing edges of said wound in said close juxtaposition; and a first removable protective member formed of a chemically inert material releasably secured to said backing member and covering said surgical adhesive and said pressure-sensitive adhesive;

whereby after removal of said protective member to expose said surgical adhesive and said pressure-sensitive adhesive, and application of said backing member with the exposed surgical adhesive pressure-sensitive adhesive onto said patient to secure the facing edges of said wound in said close juxtaposition, said surgical adhesive upon curing forms discrete bonding sites strengthening the adhesion of at least said second and third portions of said backing member to the patient and cooperating with said backing member to maintain the facing edges of said wound in said close juxtaposition without the cured adhesive adversely affecting the flexibility of said backing member.

2. A suture strip according to claim 1, wherein said backing member is formed of a chemically inert material comprising polyethylene.

3. A suture strip according to claim 2, wherein said polyethylene is a low density polyethylene.

4. A suture strip according to claim 2, wherein said polyethylene is a blend of low density polyethylene and high density polyethylene.

5. A suture strip according to claim 1, wherein said backing member is formed of a chemically inert material comprising tetrafluoroethylene.

6. A suture strip according to claim 1, wherein a plurality of spaced-apart dots of said surgical adhesive are provided only on the second and third portions of said backing member, in said discrete areas.

7. A suture strip according to claim 6, wherein the first surface of said backing member has a predetermined area and wherein said dots of surgical adhesive define a total area representing from about 10 to about 50% of said predetermined area.

8. A suture strip according to claim 6, wherein the first surface of said backing member has a predetermined area and wherein said dots of surgical adhesive define a total area representing from about 15 to about 30% of said predetermined area.

9. A suture strip according to claim 1, wherein a plurality of spaced-apart dots of said surgical adhesive are provided on the first, second and third portions of said backing member, in said discrete areas.

10. A suture strip according to claim 1, wherein a plurality of spaced-apart strips of said surgical adhesive are provided only on the second and third portions of said backing member, in said discrete areas, and wherein said strips of surgical adhesive extend transversely of said backing member.

11. A suture strip according to claim 10, wherein the first surface of said backing member has a predetermined area and wherein said strips of surgical adhesive define a total area representing from about 10 to about 50% of said predetermined area.

12. A suture strip according to claim 10, wherein the first surface of said backing member has a predetermined area and wherein said strips of surgical adhesive define a total area representing from about 15 to about 30% of said predetermined area.

13. A suture strip according to claim 1, wherein a plurality of spaced-part strips of said surgical adhesive are provided on the first, second and third portions of said backing member, in said discrete areas, and wherein said strips of surgical adhesive extend transversely of said backing member.

14. A suture strip according to claim 1, wherein said protective member comprises a film of one of polyethylene and tetrafluoroethylene.

15. A suture strip according to claim 14, wherein said polyethylene is a high density polyethylene.

16. A suture strip according to claim 1, wherein a finger-grip tab is detachably connected to said backing member at one of said ends thereof along a tear-line extending transversely of said backing member.

17. A suture strip according to claim 16, wherein said first protective member is substantially coextensive with said backing member along the length thereof and said tab, and extends beyond opposite side edges of said backing member and said tab.

18. A suture strip according to claim 1, wherein a second removable protective member is releasably secured to said backing member and covers the second surface thereof, said backing member being disposed between said first and second protective members.

19. A suture strip according to claim 18, wherein said second protective member comprises a film of one of tetrafluoroethylene and low density polyethylene.

20. A suture strip according to claim 18, wherein each of said first and second protective members extends beyond opposite end edges and opposite side edges of said backing member to define respective first and second end portions and first and second lateral portions, and wherein the first end portions and the first and second lateral portions of said first and second protective members face one another and are releasably secured together, the second end portion of said second protective member facing the second end portion of said first protective member and being partially unattached thereto so as to define with the second end portion of said first protective member a pair of finger-grip tabs.

21. A suture strip according to claim 1, wherein said surgical adhesive comprises a cyanoacrylate.

22. A suture strip according to claim 21, wherein said cyanoacrylate is 2-octylcyanoacrylate.

23. A suture strip according to claim 21, wherein said cyanoacrylate is 2-n-butylcyanoacrylate.

24. A suture strip according to claim 1, wherein said surgical adhesive comprises a cyanoacrylate in admixture with a stabilizing agent.

25. A suture strip according to claim 24, wherein said stabilizing agent is sulfurous acid.

26. A moisture-curable adhesive suture strip for closing a wound on a patient, comprising:

an elongated, flexible air-permeable backing member having opposite ends, first and second surfaces facing away from one another and a length and width adapted to secure facing edges of the wound in close juxtaposition to one another, said backing member comprising a first portion disposed between said ends and adapted to overlie the facing edges of said wound, and second and third portions disposed on either side of said first portion;

a plurality of spaced-apart rupturable spherules secured to the first surface of said backing member and disposed on at least said second and third portions thereof; said spherules each comprising a rupturable membrane formed of a chemically inert material and encapsulating a flowable, moisture-curable surgical adhesive, and being adapted to release upon rupture of said membranes said surgical adhesive onto part of the first surface of said backing member including said second and third portions thereof, in spaced-apart discrete areas of said first surface;

a pressure-sensitive adhesive on the first surface of said backing member between said spherules for adhering at least said second and third portions of said backing member to the patient with the facing edges of said wound in said close juxtaposition, prior to rupture of said spherules;

a first removable protective member releasably secured to said backing member and covering said spherules and said pressure-sensitive adhesive; and whereby after removal of said protective member to expose said spherules and said pressure-sensitive adhesive, application of said backing member with the exposed spherules and pressure-sensitive adhesive onto the patient to secure the facing edges of said wound in said close juxtaposition and application of pressure onto the second surface of said backing member to cause rupture of said spherules and release of said surgical adhesive therefrom, said surgical adhesive flows on part of the first surface of said backing member in said discrete areas and upon curing forms discrete bonding sites strengthening the adhesion of at least said second and third portions of said backing member to the patient and cooperating with said backing member to maintain the facing edges of said wound in said close juxtaposition without the cured adhesive adversely affecting the flexibility of said backing member.

27. A suture strip according to claim 26, wherein said spherules are provided only on said second and third portions of said backing member.

28. A suture strip according to claim 26, wherein said spherules are provided on said first, second and third portions of said backing member.

29. A suture strip according to claim 26, wherein said spherules are secured to the first surface of said backing member with adhesive.

30. A suture strip according to claim 29, wherein said adhesive is said pressure-sensitive adhesive.

31. A suture strip according to claim 26, wherein said backing member is formed of said chemically inert material and wherein the membrane of each said spherule is integrally formed with said backing member.

32. A suture strip according to claim 31, wherein a portion of the first surface of said backing member surrounding each said spherule is free of pressure-sensitive adhesive for receiving the surgical adhesive released from said spherule upon rupturing.

33. A suture strip according to claim 26, wherein a portion of the first surface of said backing member surrounding each said spherule is free of pressure-sensitive adhesive for receiving the surgical adhesive released from said spherule upon rupturing.

34. A suture strip according to claim 26, wherein said backing member comprises a web of fabric material.

35. A suture strip according to claim 26, wherein said backing member is formed of a polymer selected from the group consisting of polyurethane and nylon.

36. A suture strip according to claim 26, wherein said chemically inert material comprises polyethylene.

37. A suture strip according to claim 36, wherein said polyethylene is a low-density polyethylene.

38. A suture strip according to claim 36, wherein said polyethylene is a blend of low-density polyethylene and high-density polyethylene.

39. A suture strip according to claim 26, wherein said chemically inert material comprises tetrafluoroethylene.

40. A suture strip according to claim 26, wherein said spherules each have a diameter ranging from about 0.5 to about 3 mm.

41. A suture strip according to claim 40, wherein said diameter is between 1 and 2 mm.

42. A suture strip according to claim 26, wherein the first surface of said backing member has a predetermined area and wherein said spherules define a total area representing from about 10 to about 50% of said predetermined area.

43. A suture strip according to claim 26, wherein the first surface of said backing member has a predetermined area and wherein said spherules define a total area representing from about 15 to about 30% of said predetermined area.

44. A suture strip according to claim 26, wherein said protective member comprises a film of polyethylene.

45. A suture strip according to claim 44, wherein said polyethylene is a high density polyethylene.

46. A suture strip according to claim 26, wherein said first protective member comprises a sheet of wax paper.

47. A suture strip according to claim 26, wherein a finger-grip tab is detachably connected to said backing member at one of said ends thereof along a tear-line extending transversely of said backing member.

48. A suture strip according to claim 47, wherein said first protective member is substantially coextensive with said backing member along the length thereof and said tab, and extends beyond opposite side edges of said backing member and said tab.

49. A suture strip according to claim 26, wherein a second removable protective member is releasably secured to said backing member and covers the second surface thereof, said backing member being disposed between said first and second protective members.

50. A suture strip according to claim 49, wherein said second protective member comprises a film of one of tetrafluoroethylene and low density polyethylene.

51. A suture strip according to claim 49, wherein each of said first and second protective members extends beyond opposite end edges and opposite side edges of said backing member to define respective first and second end portions and first and second lateral portions, and wherein the first end portions and the first and second lateral portions of said first and second protective members face one another and are releasably secured together, the second end portion of said second protective member facing the second end portion of said first protective member and being partially unattached thereto so as to define with the second end portion of said first protective member a pair of finger-grip tabs.

52. A suture strip according to claim 26, wherein said surgical adhesive comprises a cyanoacrylate.

53. A suture strip according to claim 52, wherein said cyanoacrylate is 2-octylcyanoacrylate.

54. A suture strip according to claim 52, wherein said cyanoacrylate is 2-n-butylcyanoacrylate.

55. A suture strip according to claim 26, wherein said surgical adhesive comprises a cyanoacrylate in admixture with a stabilizing agent.

56. A suture strip according to claim 55, wherein said stabilizing agent is sulfurous acid.

57. A moisture-curable adhesive suture strip for closing a wound on a patient, comprising:

an elongated, flexible air-permeable backing member having opposite ends, first and second surfaces facing away from one another and a length and width adapted to secure facing edges of the wound in close juxtaposition to one another, said backing member comprising a first portion disposed between said ends and adapted to overlie the facing edges of said wound, and second and third portions disposed on either side of said first portion;

a pressure-sensitive adhesive on at least part of the first surface of said backing member including said second and third portions thereof, for adhering at least said second and third portions of said backing member to the patient with the facing edges of said wound in said close juxtaposition;

a first removable protective member releasably secured to said backing member and covering said pressure-sensitive adhesive, said protective member having first and second surfaces facing away from one another with the first surface facing the first surface of said backing member; and a plurality of spaced-apart rupturable spherules disposed between said backing member and said protective member and secured to the first surface of said protective member, said spherules each comprising a rupturable membrane formed of a chemically inert material and encapsulating a flowable, moisture-curable surgical adhesive, and being disposed on said protective member at predetermined locations so as to release upon rupture of said membranes said surgical adhesive onto part of the first surface of said backing member including said second and third portions thereof; in spaced-apart discrete areas of said first surface;

whereby after application of pressure onto the second surface of said backing member or said protective member to cause rupture of said spherules and release of said surgical adhesive therefrom, removal of said protective member to expose said pressure-sensitive adhesive and said surgical adhesive released on part of the first surface of said backing member in said discrete areas and application of said backing member with the exposed pressure-sensitive adhesive and surgical adhesive onto the patient to secure the facing edges of said wound in said close juxtaposition, said surgical adhesive upon curing forms discrete bonding sites strengthening the adhesion of at least said second and third portions of said backing member to the patient and cooperating with said backing member to maintain the facing edges of said wound in said close juxtaposition without the cured adhesive adversely affecting the flexibility of said backing member.

58. A suture strip according to claim 57, wherein said spherules are disposed on said protective member opposite only said second and third portions of said backing member.

59. A suture strip according to claim 57, wherein said spherules are disposed on said protective member opposite said first, second and third portions of said backing member.

60. A suture strip according to claim 57, wherein the first surface of said backing member is coated with a layer of said pressure-sensitive adhesive and wherein said spherules upon rupturing release said surgical adhesive onto the coated surface.

61. A suture strip according to claim 57, wherein a portion of the first surface of said backing member opposite each said spherule is free of pressure-sensitive adhesive for receiving the surgical adhesive released from said spherule upon rupturing.

62. A suture strip according to claim 57, wherein said spherules are secured to the first surface of said protective member with adhesive.

63. A suture strip according to claim 62, wherein said adhesive is said pressure-sensitive adhesive.

64. A suture strip according to claim 57, wherein said protective member is formed of a chemically inert material and wherein the membrane of each said spherule is integrally formed with said protective member.

65. A suture strip according to claim 64, wherein said chemically inert material comprises polyethylene.

66. A suture strip according to claim 57, wherein said chemically inert material comprises polyethylene.

67. A suture strip according to claim 66, wherein said polyethylene is a high-density polyethylene.

68. A suture strip according to claim 57, wherein said protective member comprises a film of polyethylene.

69. A suture strip according to claim 68, wherein said polyethylene is a high density polyethylene.

70. A suture strip according to claim 57, wherein said protective member comprises a sheet of wax paper.

71. A suture strip according to claim 57, wherein said backing member comprises a web of fabric material.

72. A suture strip according to claim 57, wherein said backing member is formed of a polymer selected from the group consisting of polyurethane and nylon.

73. A suture strip according to claim 57, wherein said spherules each have a diameter ranging from about 0.5 to about 3 mm.

74. A suture strip according to claim 73, wherein said diameter is between 1 and 2 mm.

75. A suture strip according to any one of claims 57 to 74, wherein the first surface of said backing member has a predetermined area and wherein said spherules define a total area representing from about 10 to about 50% of said predetermined area.

76. A suture strip according to claim 57, wherein the first surface of said backing member has a predetermined area and wherein said spherules define a total area representing from about 15 to about 30% of said predetermined area.

77. A suture strip according to claim 57, wherein a finger-grip tab is detachably connected to said backing member at one of said ends thereof along a tear-line extending transversely of said backing member.

78. A suture strip according to claim 77, wherein said first protective member is substantially coextensive with said backing member along the length thereof and said tab, and extends beyond opposite side edges of said backing member and said tab.

79. A suture strip according to claim 57, wherein a second removable protective member is releasably secured to said backing member and covers the second surface thereof, said backing member being disposed between said first and second protective members.

80. A suture strip according to claim 79, wherein said second protective member comprises a film of one of tetrafluoroethylene and low density polyethylene.

81. A suture strip according to claim 79, wherein each of said first and second protective members extends beyond opposite end edges and opposite side edges of said backing member to define respective first and second end portions and first and second lateral portions, and wherein the first end portions and the first and second lateral portions of said first and second protective members face one another and are releasably secured together, the second end portion of said second protective member facing the second end portion of said first protective member and being partially unattached thereto so as to define with the second end portion of said first protective member a pair of finger-grip tabs.

82. A suture strip according to claim 81, wherein said cyanoacrylate is 2-octylcyanoacrylate.

83. A suture strip according to claim 81, wherein said cyanoacrylate is 2-n-butylcyanoacrylate.

84. A suture strip according to claim 57, wherein said surgical adhesive comprises a cyanoacrylate.

85. A suture strip according to claim 57, wherein said surgical adhesive comprises a cyanoacrylate in admixture with a stabilizing agent.

86. A suture strip according to claim 85, wherein said stabilizing agent is sulfurous acid.

\* \* \* \* \*

UNITED STATES PATENT AND TRADEMARK OFFICE
CERTIFICATE OF CORRECTION

PATENT NO. : 6,559,350 B1
DATED : May 6, 2003
INVENTOR(S) : Stephane Tetreault et al.

It is certified that error appears in the above-identified patent and that said Letters Patent is hereby corrected as shown below:

<u>Title page,</u>
Item [57], ABSTRACT,

Replace
"A biocompatible monomer composition includes: (A) at lease one monomer, which forms a medically acceptable polymer, (B) at least one plasticizing agent present in the composition in an amount of from 0 wt. % to 15 wt. % of the composition; and (C) at least one acidic stabilizing agent having a $pK_a$, ionization constant of from about 1 to about 7. The composition can be applied to a variety of materials and is particularly suitable as in vivo tissue adhesive. A method of joining together in vivo two surfaces, e.g., body tissues, includes (a) holding damaged tissue edges together to form abutted tissue surfaces; (b) applying to the abutted tissue surfaces an excessive amount of a composition containing 1) at least one monomer, which forms a medically acceptable biodegradable polymer, 2) at least one plasticizing agent; and 3) at least one acidic stabilizing agent, and (c) maintaining the surfaces in contact until the composition polymerizes to form a thick film of polymerized composition bridging the abutted tissue surface."

with

--A moisture-curable adhesive suture strip for closing a wound on a patient, comprises an elongated, flexible air-permeable backing member formed of a chemically inert material and having opposite ends, first and second surfaces facing away from one another an a length and width sufficient to secure facing edges of the wound in close juxtaposition to one another. Variants of such a suture strip wherein the backing member has no surgical adhesive thereon and wherein a plurality of spaced-apart rupturable spherules are disposed between the backing member and the protective member are also disclosed. The spherules each comprise a rupturable membrane formed of a chemically inert material and encapsulating a flowable, moisture-curable surgical adhesive, and are adapted to release upon rupture of the membranes the surgical onto part of the first surface of the backing member including the second and third portions thereof.--

Signed and Sealed this

Twelfth Day of October, 2004

JON W. DUDAS
*Director of the United States Patent and Trademark Office*